(12) United States Patent
Kodama et al.

(10) Patent No.: US 11,963,660 B2
(45) Date of Patent: Apr. 23, 2024

(54) DISTAL END UNIT OF ENDOSCOPE, AND ENDOSCOPE

(71) Applicant: OLYMPUS CORPORATION, Tokyo (JP)

(72) Inventors: Daichi Kodama, Hachioji (JP); Hiroyuki Motohara, Hachioji (JP); Hiroyuki Nagamizu, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 263 days.

(21) Appl. No.: 17/401,989

(22) Filed: Aug. 13, 2021

(65) Prior Publication Data
US 2021/0369087 A1 Dec. 2, 2021

Related U.S. Application Data

(63) Continuation of application No. PCT/JP2019/011111, filed on Mar. 18, 2019.

(51) Int. Cl.
*A61B 1/00* (2006.01)
*A61B 1/05* (2006.01)
(Continued)

(52) U.S. Cl.
CPC .......... *A61B 1/00096* (2013.01); *A61B 1/051* (2013.01); *A61B 1/07* (2013.01); *G02B 23/243* (2013.01)

(58) Field of Classification Search
CPC ....... A61B 1/00096; A61B 1/05; A61B 1/051; A61B 1/053; G02B 7/02; G02B 7/025
See application file for complete search history.

(56) References Cited

U.S. PATENT DOCUMENTS 5,536,244 A * 7/1996 Muller .................... A61L 29/02
600/133
2001/0033436 A1* 10/2001 Hunter ................... G02B 7/026
359/811
(Continued)

FOREIGN PATENT DOCUMENTS

EP 3 213 667 A1 9/2017
JP 2000-051142 A 2/2000
(Continued)

OTHER PUBLICATIONS

International Search Report dated Jun. 11, 2019 received in PCT/JP2019/011111.
English language abstract only of US 2012/183288 A1.

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

A distal end unit of an endoscope includes: a distal end frame body that is constituted by a resin molded article configuring a molded interconnect device, that is provided with an image pickup unit containing room, and that is provided with an observation opening portion that opens the image pickup unit containing room on a distal end surface exposed to an exterior; a metal layer that is provided along a flat surface of the observation opening portion; a cover glass that closes the observation opening portion; a solder layer that is bonded to the metal layer and that holds the cover glass on the distal end frame body; and an adhesive layer that covers the solder layer, the metal layer is provided at a position corresponding to a groove provided on the flat surface, and the solder layer is disposed in an interior of the groove.

20 Claims, 19 Drawing Sheets

(51) Int. Cl.
*A61B 1/07* (2006.01)
*G02B 23/24* (2006.01)

(56) References Cited

U.S. PATENT DOCUMENTS

| | | | | |
|---|---|---|---|---|
| 2002/0186478 | A1* | 12/2002 | Watanabe | G02B 23/243 359/811 |
| 2010/0022841 | A1* | 1/2010 | Takahashi | A61B 1/127 600/162 |
| 2010/0152540 | A1 | 6/2010 | Tanoue | |
| 2012/0123210 | A1* | 5/2012 | Eisenkolb | A61B 1/0011 65/42 |
| 2015/0062316 | A1* | 3/2015 | Haraguchi | A61B 1/00165 359/513 |
| 2015/0065796 | A1* | 3/2015 | Iwane | A61B 1/0011 600/109 |
| 2017/0265715 | A1 | 9/2017 | Nishina et al. | |

FOREIGN PATENT DOCUMENTS

| | | | | |
|---|---|---|---|---|
| JP | 2000-193892 | A | | 7/2000 |
| JP | 2000193892 | A | * | 7/2000 |
| JP | 2003-000526 | A | | 1/2003 |
| JP | 2003169775 | A | * | 6/2003 |
| JP | 2003-304056 | A | | 10/2003 |
| JP | 2005-040162 | A | | 2/2005 |
| JP | 2006-223763 | A | | 8/2006 |
| JP | 2006223763 | A | * | 8/2006 |
| JP | 2009-201762 | A | | 9/2009 |
| JP | 4924777 | B2 | | 4/2012 |
| JP | 2013-198566 | A | | 10/2013 |
| JP | 2017-505154 | A | | 2/2017 |
| JP | 2017-113417 | A | | 6/2017 |
| JP | 2017-209278 | A | | 11/2017 |
| JP | 2018-120005 | A | | 8/2018 |
| WO | 2006/095490 | A1 | | 9/2006 |
| WO | WO-2013128681 | A1 | * | 9/2013 ......... A61B 1/00096 |
| WO | 2016/203830 | A1 | | 12/2016 |

* cited by examiner

DISTAL END UNIT OF ENDOSCOPE, AND ENDOSCOPE

CROSS REFERENCE TO RELATED APPLICATION

This application is a continuation application of PCT/JP2019/011111 filed on Mar. 18, 2019, the entire contents of which are incorporated herein by this reference.

BACKGROUND OF THE INVENTION

1. Field of the Invention

The present invention relates to a distal end unit of an endoscope in which an optical member such as an observation window is disposed on an exposed surface exposed to an exterior, and the endoscope.

2. Description of the Related Art

Conventionally, in a medical field or an industrial field, an endoscope has been widely used, for observing sites for which it is difficult to directly perform visual observation, for example, an interior of a living body, a structural object or the like. The endoscope is formed such that the endoscope can be introduced from an exterior to the interior of the living body or the structural object, and is configured such that the endoscope can form an optical image or can pick up the optical image.

In the endoscope, a distal end portion provided at a distal end of an insertion portion is mainly configured by a distal end unit in which various functional components are provided in a rigid distal end frame. In this kind of distal end unit, for example, as disclosed in Japanese Patent Application Laid-Open Publication No. 2000-193892, the distal end frame (distal end portion body) includes an image pickup apparatus attachment hole and an illumination hole. An image pickup unit including an objective lens system on a distal end side is attached to the image pickup apparatus attachment hole. In this case, the objective lens system configuring the image pickup unit is held by a lens frame, in a state where a first lens having a front surface exposed to an exterior is fixed to the lens frame in an airtight manner by soldering. Further, an illumination lens is fixed to the illumination hole in an airtight manner by soldering. Note that a purpose of the airtight structure using solder is, for example, to secure durability against cleaning under high temperature and pressure, as exemplified by autoclave sterilization.

SUMMARY OF THE INVENTION

A distal end unit of an endoscope according to an aspect of the present invention includes: a distal end frame body constituted by a resin molded article, the resin molded article configuring a molded interconnect device in which a metal plating pattern is formed on a surface of the resin molded article, the distal end frame body being provided with a containing room that contains a functional component in an interior and being provided with an opening that opens the containing room on an exposed surface exposed to an exterior; a metal layer constituted by the metal plating pattern configuring the molded interconnect device and provided along the opening in an interior region of the opening; an optical member closing the opening; a solder layer bonded to the metal layer and holding the optical member on the distal end frame body; and an adhesive layer covering the solder layer between the distal end frame body and the optical member, in which the opening includes a first inner circumference surface, a second inner circumference surface, a flat surface and a groove, the first inner circumference surface being adjacent to the exposed surface, the second inner circumference surface being formed at a position further away from the exposed surface in a depth direction than the first inner circumference surface and having an inner circumference length shorter than an inner circumference length of the first inner circumference surface, the flat surface being formed between the first inner circumference surface and the second inner circumference surface, the groove being provided on the flat surface, the metal layer is provided at a position corresponding to the groove, and the solder layer is disposed in an interior of the groove.

An endoscope according to an aspect of the present invention includes a distal end unit including: a distal end frame body constituted by a resin molded article, the resin molded article configuring a molded interconnect device in which a metal plating pattern is formed on a surface of the resin molded article, the distal end frame body being provided with a containing room that contains a functional component in an interior and being provided with an opening that opens the containing room on an exposed surface exposed to an exterior; a metal layer constituted by the metal plating pattern configuring the molded interconnect device and provided along the opening in an interior region of the opening; an optical member closing the opening; a solder layer bonded to the metal layer and holding the optical member on the distal end frame body; and an adhesive layer covering the solder layer between the distal end frame body and the optical member, the opening including a first inner circumference surface, a second inner circumference surface, a flat surface and a groove, the first inner circumference surface being adjacent to the exposed surface, the second inner circumference surface being formed at a position further away from the exposed surface in a depth direction than the first inner circumference surface and having an inner circumference length shorter than an inner circumference length of the first inner circumference surface, the flat surface being formed between the first inner circumference surface and the second inner circumference surface, the groove being provided on the flat surface, the metal layer being provided at a position corresponding to the groove, the solder layer being disposed in an interior of the groove, and an insertion portion in which the distal end unit is provided.

DETAILED DESCRIPTION OF THE PREFERRED EMBODIMENTS

Figure 1:
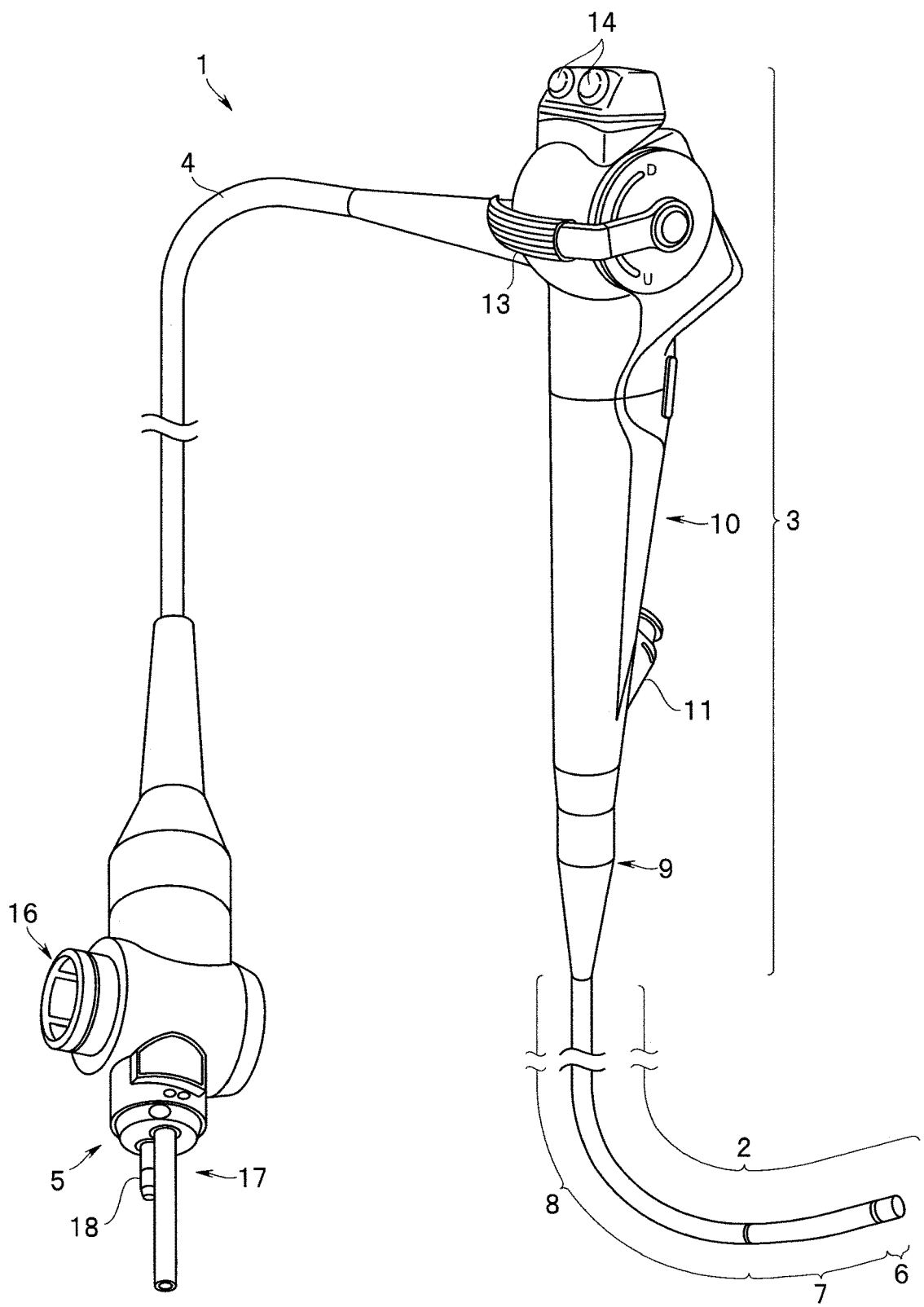
FIG. 1 is an external perspective view of an endoscope.

Embodiments of the present invention will be described below with reference to the drawings. FIG. 1 to FIG. 5 are diagrams according to an embodiment of the present invention, and FIG. 1 is an external perspective view of an endoscope.

An endoscope 1 shown in FIG. 1 is configured to include an elongated insertion portion 2 that is inserted into a body cavity of a subject, an operation portion 3 that is provided so as to be continuous with a proximal end of the insertion portion 2, a universal cable 4 that extends from a proximal end of the operation portion 3, and an endoscope connector 5 that is arranged at an extension end of the universal cable 4.

The insertion portion 2 is a tubular member in which a distal end portion 6, a bending portion 7 and a flexible tube portion 8 are provided so as to be continuous in this order from a distal end side and that has flexibility.

Figure 2:
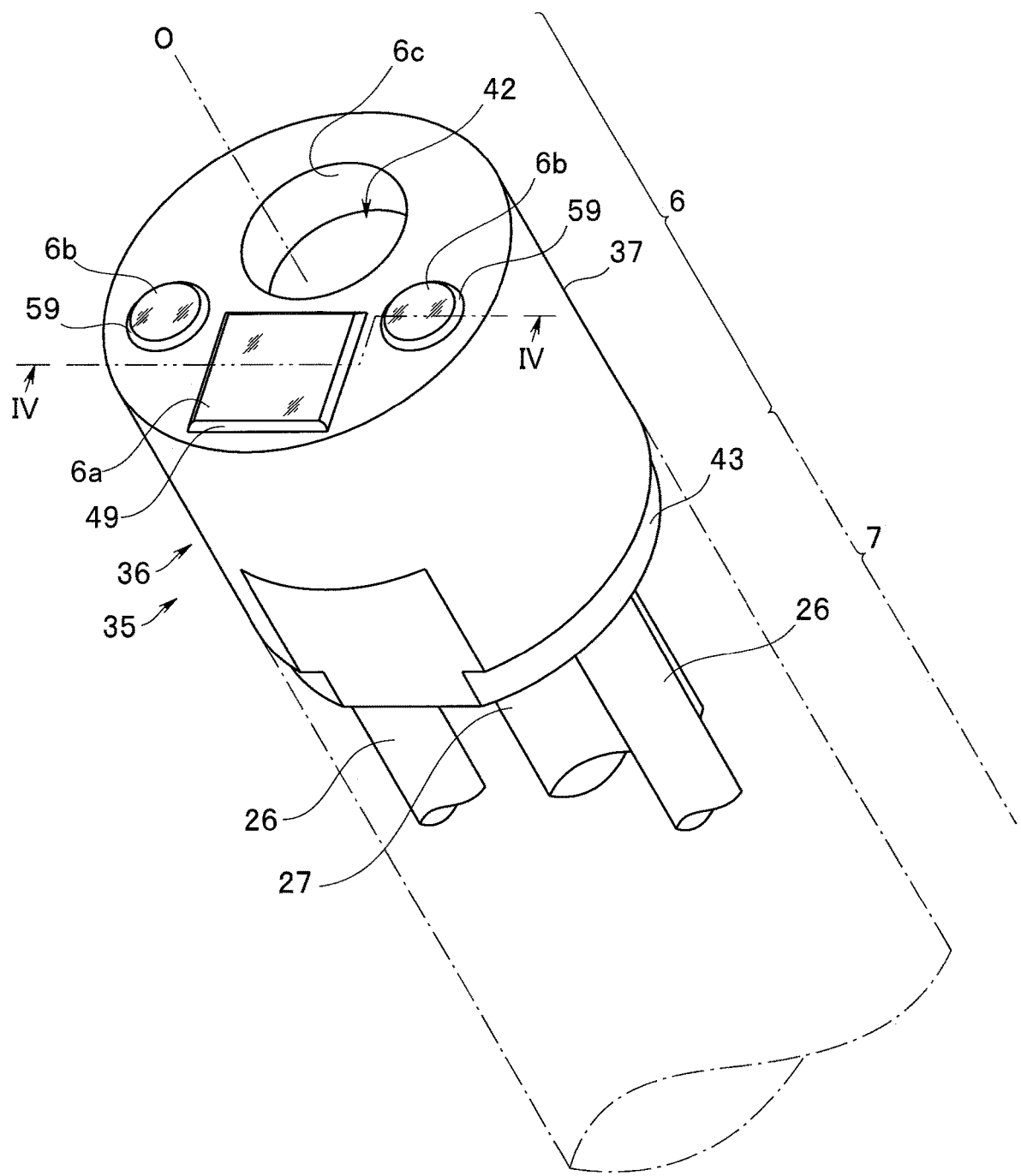
FIG. 2 is a perspective view of a distal end unit.

As shown in FIG. 2, on a distal end surface of the distal end portion 6, for example, an observation window 6a for observing a subject, a pair of illumination windows 6b for emitting illumination light to the subject, and a channel opening portion 6c that communicates with a distal end side of a treatment instrument channel 27 are arranged.

Figure 4:
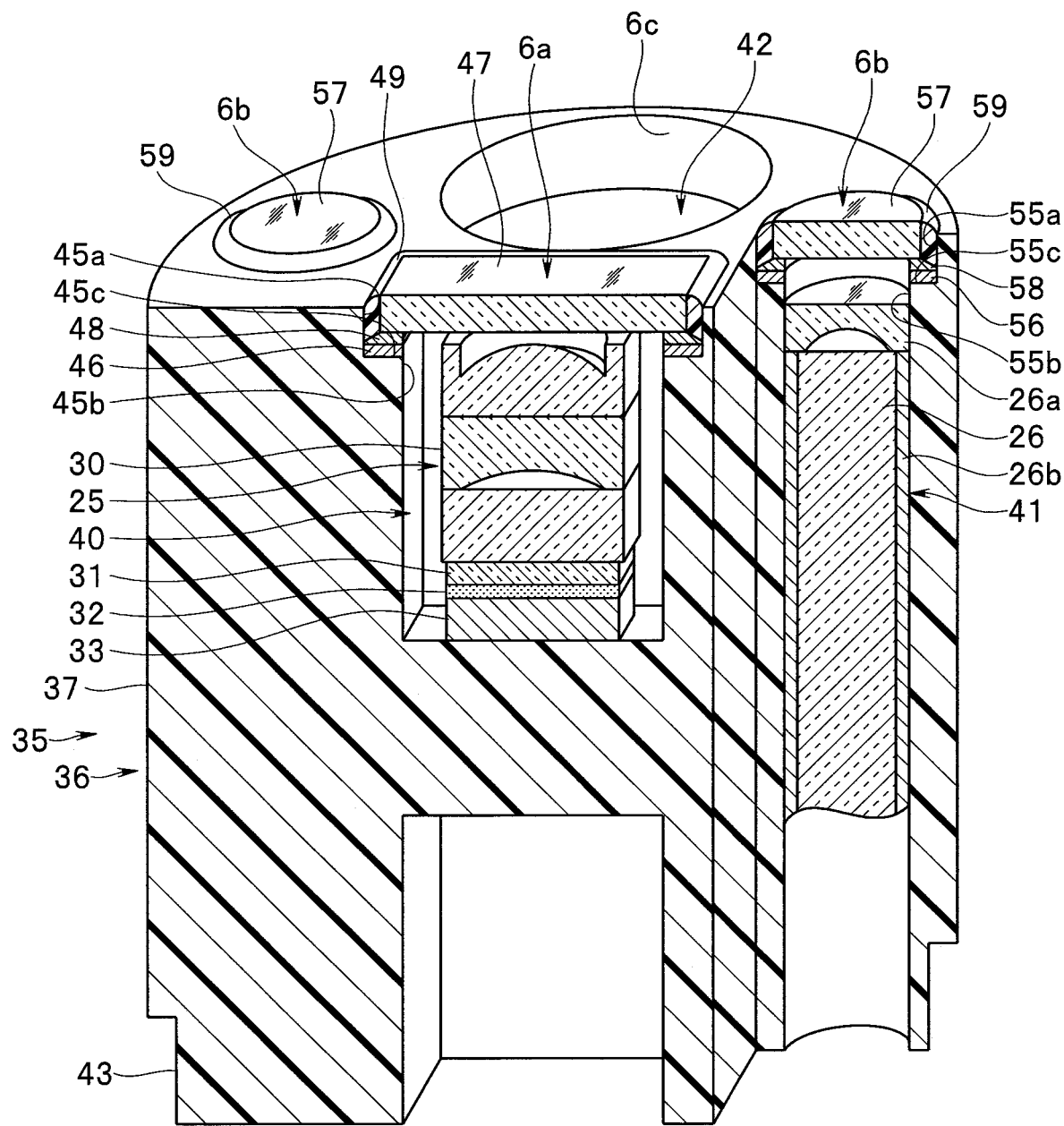
FIG. 4 is a perspective cross-sectional view taken along line IV-IV in FIG. 2.
Figure 5:
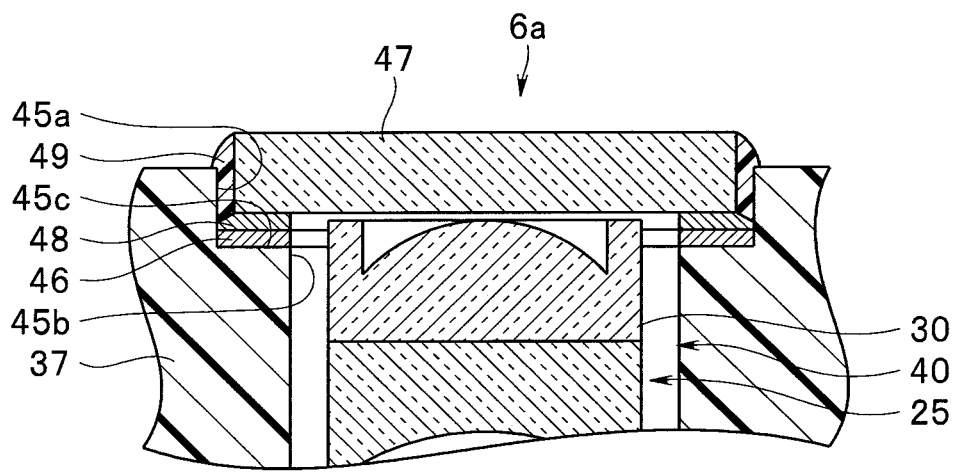
FIG. 5 is a cross-sectional view showing a holding structure of an observation window.

As shown in FIG. 4, an image pickup unit 25, a light guide 26, and the like are arranged in an interior of the distal end portion 6. The image pickup unit 25 picks up an optical image of the subject through the observation window 6a, and the light guide 26 guides the illumination light to be emitted to the subject through the illumination window 6h, to the distal end portion 6.

Note that the endoscope 1 is not limited to an electronic endoscope including the image pickup unit at the distal end portion 6 but may be a fiberscope in which an image guide fiber is arranged at the insertion portion 2.

For example, the bending portion 7 is a mechanism site configured such that the bending portion 7 can be actively bent in two bending directions of an upward direction and a downward direction (UP-DOWN). Note that an upward direction, a downward direction, a right direction and a left direction for the insertion portion 2 and the like are conveniently defined so as to correspond to an upward direction, a downward direction, a right direction and a left direction in an endoscope image that is picked up by the image pickup unit 25 in the embodiment.

The flexible tube portion 8 is a tubular member configured to have flexibility such that the flexible tube portion 8 can be passively bent. Various signal cables extending from the image pickup unit 25 and the like, the light guide 26 and the like are inserted into an interior of the flexible tube portion 8, in addition to the treatment instrument channel 27.

The operation portion 3 is configured to include a bend preventing portion 9 that is connected to the flexible tube portion 8 so as to cover a proximal end of the flexible tube portion 8, and a grasping portion 10 that is provided so as to be continuous with a proximal end side of the bend preventing portion 9 and that can be grasped by user's hand.

A treatment instrument insertion portion 11 that communicates with a proximal end side of the treatment instrument channel 27 is provided on a distal end side of the grasping portion 10. Further, an operation lever 13 for performing a bending operation of the bending portion 7 and operation switches 14 to which various functions of the endoscope 1 are assigned are provided on a proximal end side of the grasping portion 10.

For example, the universal cable 4 is a composite cable that allows insertion of various signal lines, the light guide 26 and the like in an interior and that allows insertion of an air/water feeding tube (not illustrated) and the like in the interior. The various signal lines extend from the distal end portion 6 of the insertion portion 2, and a distal end side of the air/water feeding tube is connected to the treatment instrument channel 27.

The endoscope connector 5 is configured to include an electric connector portion 16 for connecting various signal lines 21 to a video processor (not illustrated) that is an external apparatus, a light source connector portion 17 for connecting a light guide bundle 22 to a light source apparatus (not illustrated) that is an external apparatus, and an air/water feeding plug 18 for connecting the air/water feeding tube to an air/water feeding apparatus (not illustrated) that is an external apparatus.

Next, a configuration of the distal end portion 6 will be more specifically described with reference to FIG. 2 to FIG. 6.

The distal end portion 6 in the embodiment is mainly configured by a distal end unit 35. In the distal end unit 35, various functional components such as the image pickup unit 25 are provided in a rigid distal end frame 36 constituted by a molded interconnect device (MID).

Figure 3:
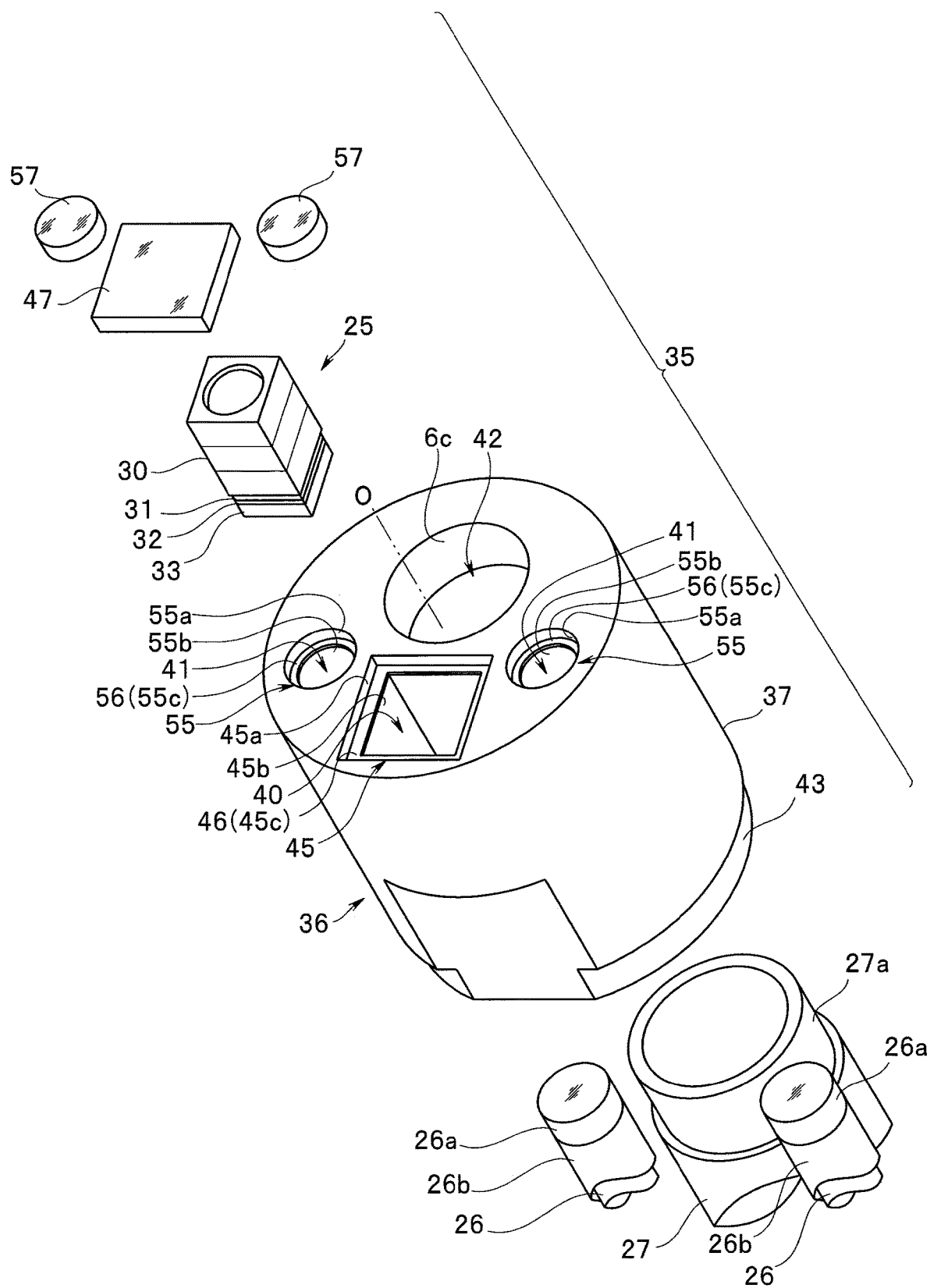
FIG. 3 is an exploded perspective view of the distal end unit.

In the embodiment, the image pickup unit 25 is provided in the distal end frame 36 as a functional component, and for example, is configured by a CSP (chip size package) in which an image-pickup lens unit 30, a cover glass 31, and an image pickup device 33 stuck to the cover glass 31 through an adhesion layer 32 are integrally packaged, as shown in FIG. 3 and FIG. 4. The image-pickup lens unit 30 is constituted by a lens stack body made using a wafer level optics technique. The image-pickup lens unit 30 in the image pickup unit 25 is produced by making a plurality of lens wafers in each of which a lens is formed on a base material such as a glass substrate and stacking and dicing the lens wafers, for example. Therefore, the image-pickup lens unit 30 in the embodiment is a lens unit that has a rectangular shape in planar view and that has no lens frame. Further, the image pickup device 33 is also formed in a rectangular shape in planar view, by dicing or the like, and therefore, the image pickup unit 25 in the embodiment has a roughly rectangular parallelepiped shape as a whole.

For example, the distal end frame 36 includes a distal end frame body 37 formed by injection molding using a resin material and having a roughly circular columnar shape. In the distal end frame body 37, a distal end surface and a roughly whole range of an outer circumference surface are exposed on a surface of the distal end portion 6, and directly form an external shape of the distal end portion 6. Therefore, as the resin material composing the distal end frame body 37, a material having not only compatibility with the MID technique but also biological compatibility is selected. In the embodiment, the distal end frame body 37 means a resin portion formed by injection molding, and various wiring patterns, metal layers 46, 56 (described later) and the like are formed on a surface of the distal end frame body 37 by metal patterns using the MID technique, so that the distal end frame 36 is configured.

In an interior of the distal end frame body 37, an image pickup unit containing room 40, a light source containing room 41 and a channel holding room 42 are formed. The image pickup unit containing room 40 serves as a containing room that contains the image pickup unit 25 that is an optical functional component. The light source containing room 41 serves as containing room that contains a distal end side of the light guide 26 as a light source that is an optical functional component. The channel holding room 42 is a room for holding a distal end side of the treatment instrument channel 27. Furthermore, a connection step portion 43 for connection to the bending portion 7 is formed on an outer circumference of a proximal end side of the distal end frame body 37.

For example, the image pickup unit containing room 40 is configured by a bottomed hole that extends in a direction of an insertion axis O of the insertion portion 2. The image pickup unit containing room 40 corresponds to the image pickup unit 25 having a roughly rectangular parallelepiped shape, and is a rectangular hole in which a section shape in a direction orthogonal to the insertion axis O is a roughly rectangular shape.

In the image pickup unit containing room 40, the image pickup unit 25 is contained. The image pickup device 33 is electrically connected to a wiring pattern (not illustrated) formed on a bottom surface of the image pickup unit containing room 40 by soldering or the like, so that the image pickup unit 25 is fixed.

Further, an observation opening portion 45 is formed on a distal end side of the image pickup unit containing room 40. The observation opening portion 45 opens the image pickup unit containing room 40 on a distal end surface that is an exposed surface of the distal end frame body 37.

The observation opening portion 45 is configured by a stepped opening including a first inner circumference surface 45a adjacent to the distal end surface of the distal end frame body 37, a second inner circumference surface 45b formed at a position further away from the distal end surface in a depth direction than the first inner circumference surface 45a (namely, a position closer to the proximal end than the first inner circumference surface 45a) and having an inner circumference length shorter than an inner circumference length of the first inner circumference surface 45a, and a flat surface 45c formed between the first inner circumference surface 45a and the second inner circumference surface 45b.

The first inner circumference surface 45a and the second inner circumference surface 45b correspond to a shape of the image pickup unit containing room 40 and are provided so as to have roughly rectangular shapes in planar view. Note that the second inner circumference surface 45b is on a plane identical to an inner circumference surface of the image pickup unit containing room 40 in the embodiment.

The metal layer 46 constituted by a metal plating pattern such as a copper plating pattern is provided on the flat surface 45c of the observation opening portion 45. In other words, the metal layer 46 is provided along the observation opening portion 45 in an interior of the observation opening portion 45. The metal layer 46 is formed by the MID technique, and for example, is formed by activating a resin surface forming the flat surface 45c by laser irradiation or the like and then performing metal plating to the resin surface after the activation.

In the observation opening portion 45, a cover glass 47 is disposed inside the first inner circumference surface 45a. The cover glass 47 is an optical member for forming the observation window 6a. A metallization treatment for bonding is performed to a partial region of the cover glass (not illustrated). A solder layer 48 is formed between the cover glass 47 and the metal layer 46, and the cover glass 47 is held by the distal end frame body 37 (observation opening portion 45) through the solder layer 48.

More specifically, in an attaching process for the cover glass 47, solder is disposed between the cover glass 47 and the metal layer 46. The solder is inched by reflow, laser irradiation or the like, and thereby, the solder layer 48 is formed between the cover glass 47 and the metal layer 46. The solder layer 48 bonds the cover glass 47 and the metal layer 46, and thereby, the cover glass 47 is held by the metal layer 46 through the solder layer 48.

Further, by the bonding through the solder layer 48, the cover glass 47 seals the image pickup unit containing room 40 in an airtight manner, and forms the observation window 6a on the distal end surface of the distal end frame 36.

Furthermore, the space between an outer circumference surface of the cover glass 47 and the first inner circumference surface 45a is filled with a resin adhesive, and by an adhesive layer 49 formed by the resin adhesive, the solder layer 48 is prevented from being exposed on the surface of the distal end frame 36.

For example, the light source containing room 41 is configured by a through-hole that extends in the direction of the insertion axis O of the insertion portion 2. The light source containing room 41 is a circular hole in which a section shape in a direction orthogonal to the insertion axis O is a roughly circular shape.

The light guide 26 is inserted into the light source containing room 41. More specifically, the light guide 26 is inserted into the light source containing room 41, in a state where an illumination lens 26a is attached to a distal end and an outer circumference is covered by a pipe sleeve 26b. Then, the light guide 26 is fixed, for example, by adhesion of the pipe sleeve 26b to an inner circumference surface of the light source containing room 41.

Further, an illumination opening portion 55 is formed on a distal end side of the light source containing room 41. The illumination opening portion 55 opens the light source containing room 41 on the distal end surface that is the exposed surface of the distal end frame body 37.

The illumination opening portion 55 is configured by a stepped opening including a first inner circumference surface 55a adjacent to the distal end surface of the distal end frame body 37, a second inner circumference surface 55b formed at a position further away from the distal end surface in a depth direction than the first inner circumference surface 55a (namely, a position closer to the proximal end than the first inner circumference surface 55a) and having an inner circumference length shorter than an inner circumference length of the first inner circumference surface 55a, and a flat surface 55c formed between the first inner circumference surface 55a and the second inner circumference surface 55b.

The first inner circumference surface 55a and the second inner circumference surface 55b correspond to a shape of the light source containing room 41 and are provided so as to have roughly circular shapes in planar view. Note that the second inner circumference surface 55b is on a plane identical to an inner circumference surface of the light source containing room 41 in the embodiment.

The metal layer 56 constituted by a copper plating pattern is provided on the flat surface 55c of the illumination opening portion 55, by the MID technique. In other words, the metal layer 56 is provided along the illumination opening portion 55 in an interior of the illumination opening portion 55.

In the illumination opening portion 55, an optical member 57 for forming the illumination window 6h is disposed inside the first inner circumference surface 55a. A solder layer 58 is formed between the cover glass 57 and the metal layer 56, and the cover glass 57 is held by the distal end frame body 37 (illumination opening portion 55) through the solder layer 58.

Further, by the bonding through the solder layer 58, the cover glass 57 seals the light source containing room 41 in an airtight manner, and forms the illumination window 6b on the distal end surface of the distal end frame 36.

Furthermore, the space between an outer circumference surface of the cover glass 57 and the first inner circumference surface 55a is filled with a resin adhesive, and by an adhesive layer 59 formed by the resin adhesive, the solder layer 58 is prevented from being exposed on the surface of the distal end frame 36.

The channel holding room 42 is configured by a through-hole that extends in the direction of the insertion axis O of the insertion portion 2. The channel holding room 42 is a circular hole in which a section shape in a direction perpendicular to the insertion axis O is a roughly circular shape.

The treatment instrument channel 27 is held in the channel holding room 42. More specifically, a pipe sleeve 27a is inserted into an inner circumference of a distal end of the treatment instrument channel 27, and the pipe sleeve 27a is inserted into the channel holding room 42, for example, to adhere to an inner circumference surface of the channel holding room 42, so that the treatment instrument channel 27 is fixed.

The channel opening portion 6c is formed on a distal end side of the channel holding room 42.

According to the embodiment, it is possible to provide the distal end unit 35 of the endoscope f that has a good workability and that allows reduction in diameter by a simple configuration, by including: the distal end frame body 37 that is constituted by the resin molded article configuring the molded interconnect device, that is provided with the image pickup unit containing room 40 that contains the image pickup unit 25 in the interior and the light source containing room 41 that contains the light guide 26, and that is provided with the observation opening portion 45 that opens the image pickup unit containing room 40 on the distal end surface exposed to the exterior and the illumination opening portion 55 that opens the light source containing room 41 on the distal end surface; the metal layers 46, 56 that are constituted by the metal plating patterns (for example, copper plating patterns) configuring the molded interconnect device and that are provided along the flat surface 45c of the observation opening portion 45 and the flat surface 55c of the illumination opening portion 55; the cover glasses 47, 57 that close the observation opening portion 45 and the illumination opening portion 55; the solder layers 48, 58 that are bonded to the metal layers 46, 56 and that hold the cover glasses 47, 57 on the distal end frame body 37; and the adhesive layers 49, 59 that cover the solder layers 48, 58 between the distal end frame body 37 and the cover glasses 47, 57.

In other words, the distal end frame 36 in the embodiment is configured such that the metal layers 46, 56 and others are provided at proper positions in the distal end frame body 37 made of resin, and therefore, it is possible to realize a higher workability compared to distal end frames made of metal. Particularly, by employing the distal end frame body 37 made of resin, it is possible to easily form, for example, the image pickup unit containing room 40 that has a rectangular section and that contains the image pickup unit 25 having a roughly rectangular parallelepiped shape as a whole.

Further, by adopting the distal end frame body 37 made of resin, it is not necessary to perform a special countermeasure for high-frequency current and the like that are emitted from various treatment instruments such as a diathermy knife, for example, it is not necessary to provide a separate distal end cover made of resin, so that it is possible to realize simplification of structure and reduction in the number of components.

Furthermore, by excluding components such as the distal end cover, it is possible to effectively realize reduction in the diameter of the distal end portion 6.

In addition, by providing the metal layers 46, 56 at proper positions in the distal end frame body 37 using the MID technique, it is possible to solder the cover glasses 47, 57 configuring the observation window 6a and the illumination window 6b, to the distal end frame 36, and it is possible to secure durability of the airtight structure against cleaning under high temperature and pressure, as exemplified by autoclave sterilization. Furthermore, since the solder layers 48, 58 are covered by the adhesive layers 49, 59, it is possible to adequately prevent contact of the solder layers 48, 58 with a human body and the like, even in the configuration in which the distal end cover and the like are excluded.

In the embodiment, various modification can be made for the disposition of the metal layers and the like. Note that examples of the disposition of the metal layer 46 and the like in the observation opening portion 45 will be mainly described below, but needless to say, similar modifications can also be made for the disposition of the metal layer 56 and the like in the illumination opening portion 55.

Figure 6:
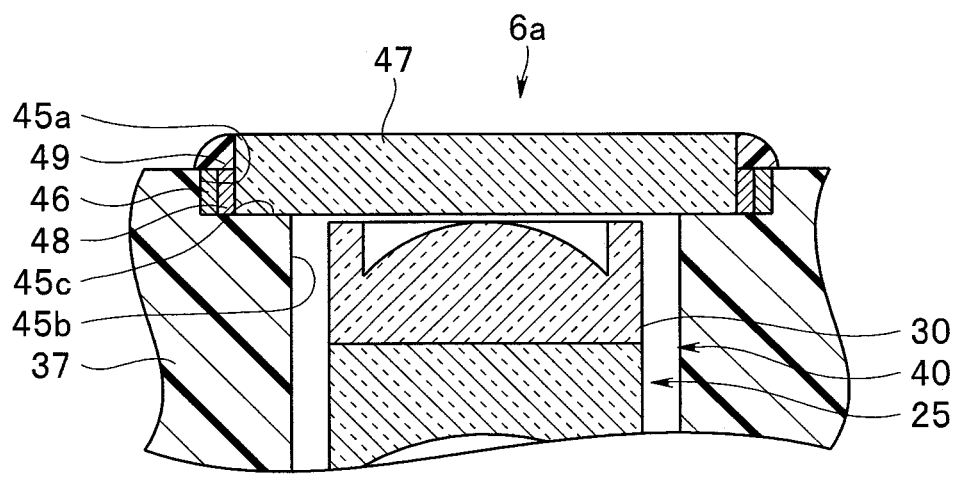
FIG. 6 is a cross-sectional view showing a holding structure of an observation window according to a first modification.

For example, as shown in FIG. 6, the metal layer 46 can be formed on the first inner circumference surface 45a of the observation opening portion 45. In this case, for example, the solder layer 48 can be formed between the cover glass 47 and the first inner circumference surface 45a, and the adhesive layer 49 can be formed on the distal end surface of the distal end frame body 37.

Figure 7:
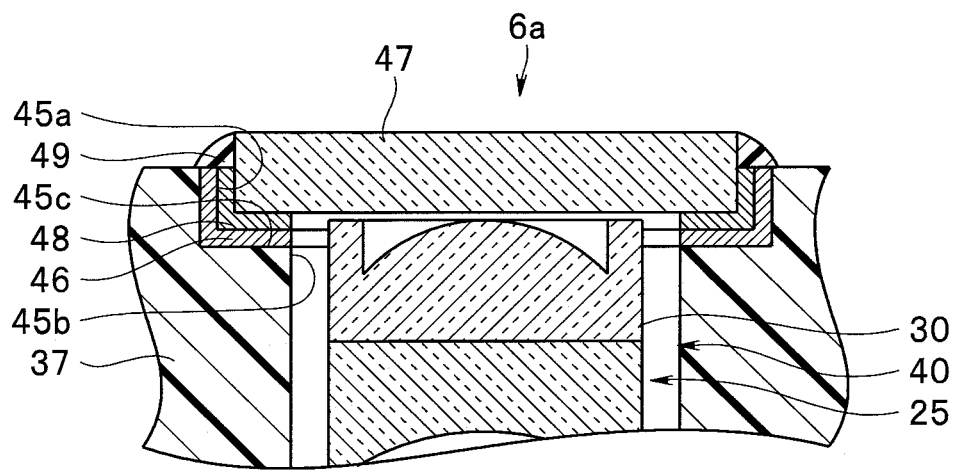
FIG. 7 is a cross-sectional view showing a holding structure of an observation window according to a second modification.

For example, as shown in FIG. 7, the metal layer 46 can be formed on the first inner circumference surface 45a and flat surface 45c of the observation opening portion 45. In this case, for example, the solder layer 48 can be formed between the cover glass 47 and the two surfaces, i.e., the first inner circumference surface 45a and the flat surface 45c, and the adhesive layer 49 can be formed on the distal end surface of the distal end frame body 37.

Figure 8:
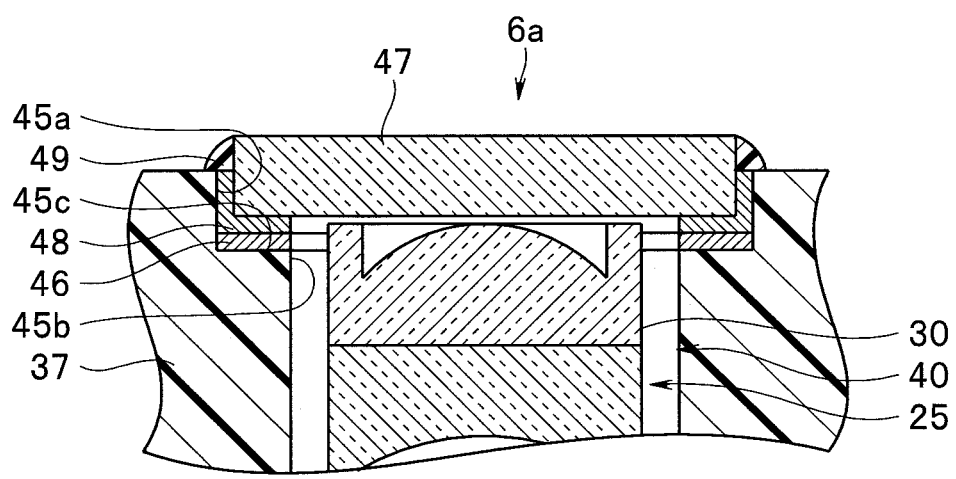
FIG. 8 is a cross-sectional view showing a holding structure of an observation window according to a third modification.

For example, as shown in FIG. 8, the metal layer 46 can be formed on only the flat surface 45c of the observation opening portion 45, and the solder layer 48 can be formed between the cover glasses 47 and the two surfaces, i.e., the first inner circumference surface 45a and the flat surface 45c. In this case, for example, the adhesive layer 49 can be formed on the distal end surface of the distal end frame body 37.

Figure 9:
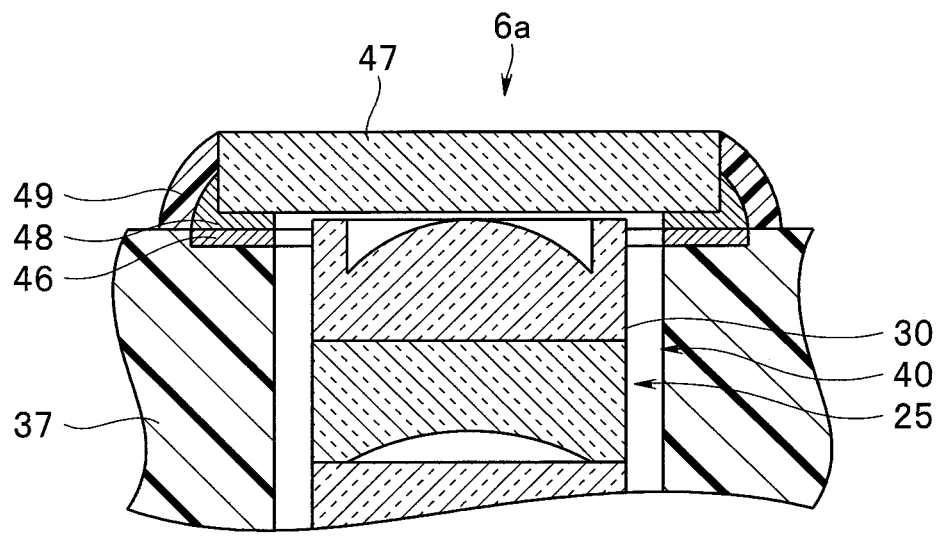
FIG. 9 is a cross-sectional view showing a holding structure of an observation window according to a fourth modification.

For example, as shown in FIG. 9, the metal layer 46 can be provided on the distal end surface of the distal end frame body 37, so as to surround the observation opening portion 45. In this case, the solder layer 48 and the adhesive layer 49 can be formed on the distal end surface of the distal end frame body 37. Note that the stepped structure constituted by the first and second inner circumference surfaces 45a, 45b and the flat surface 45c can be excluded and the observation opening portion 45 can be constituted by a single inner circumference surface in the modification.

Figure 10:
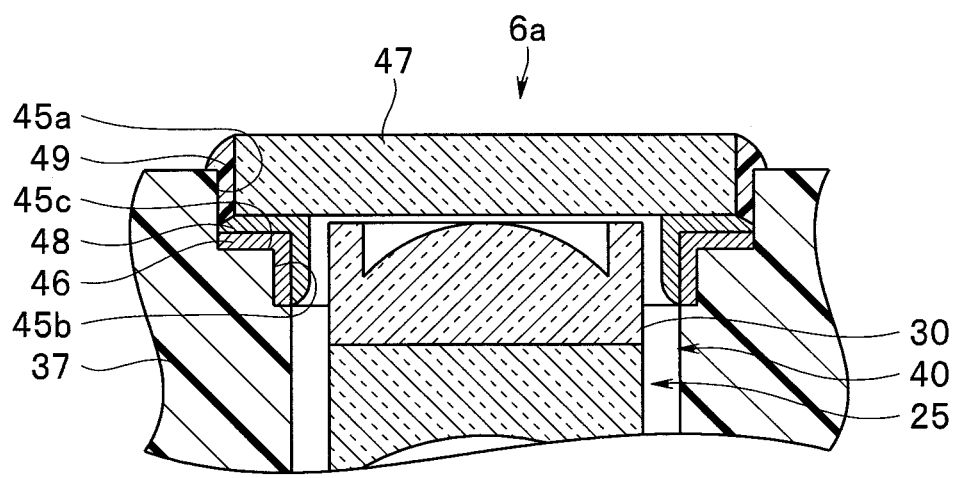
FIG. 10 is a cross-sectional view showing a holding structure of an observation window according to a fifth modification.

For example, as shown in FIG. 10, the metal layer 46 can be formed on the second inner circumference surface 45b and the flat surface 45c. In this case, for example, the solder layer 48 is formed from between the cover glass 47 and the flat surface 45c to an inside of the second inner circumference surface 45b, and the adhesive layer 49 can be formed between the cover glass 47 and the first inner circumference surface 45a.

Figure 11:
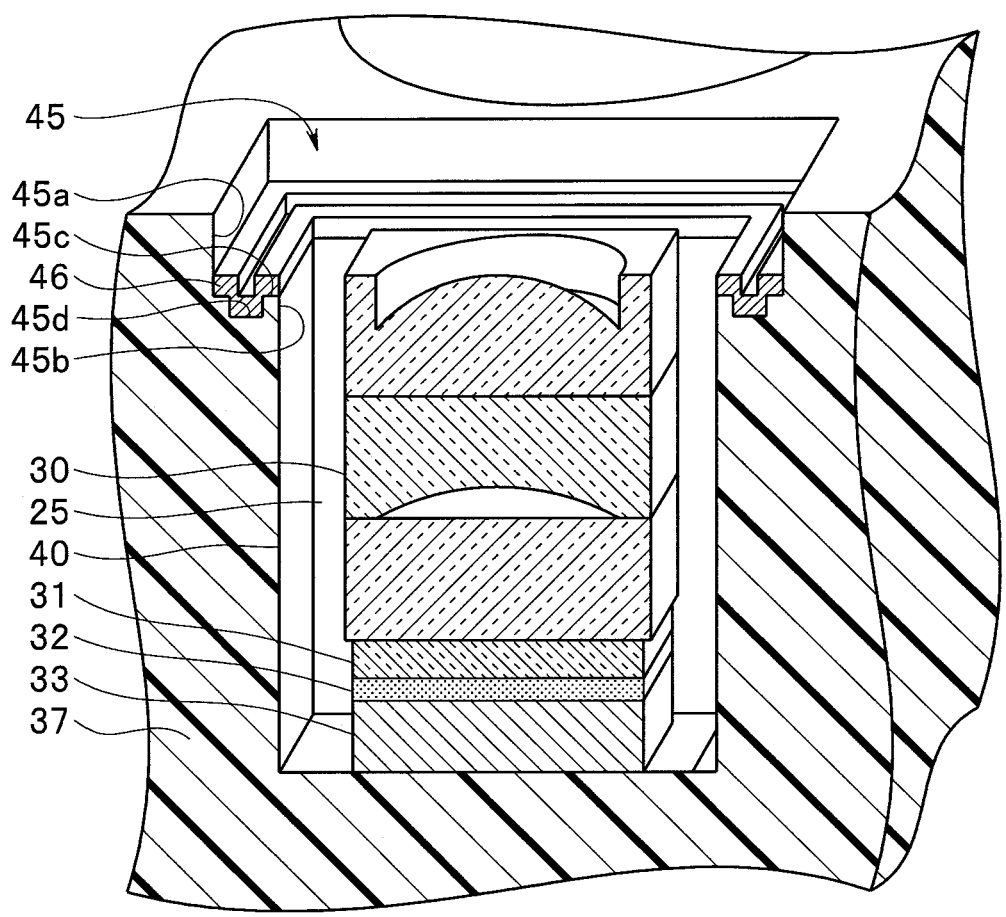
FIG. 11 is a perspective view showing a principal part of a distal end frame according to a sixth modification.
Figure 12:
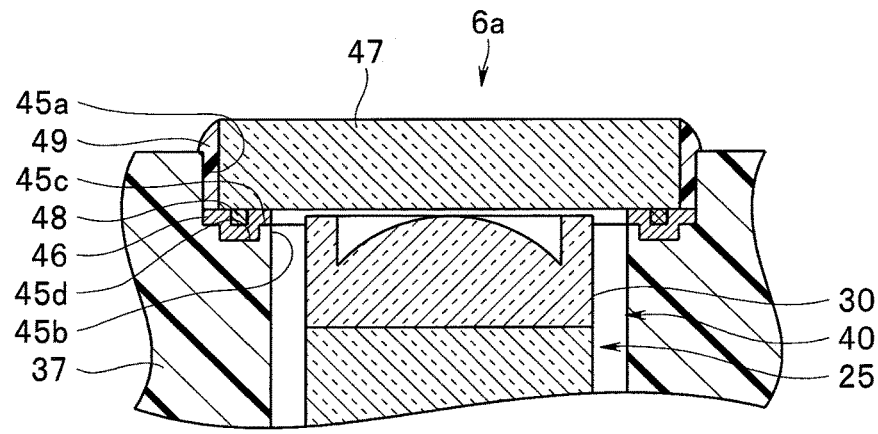
FIG. 12 is a cross-sectional view showing a holding structure of an observation window according to the sixth modification.

For example, as shown in FIG. 11 and FIG. 12, a groove portion 45d as a groove can be provided on the flat surface 45c, and the metal layer 46 can be formed on a region that is on the flat surface 45c and that corresponds to the groove portion 45d. By this configuration, it is possible to prevent molten solder from flowing into the image pickup unit containing room 40 when the solder layer 48 is formed on the metal layer 46.

Further, it is possible to cause the cover glass 47 to abut on the flat surface 45c through the metal layer 46, and therefore, it is possible to easily perform positioning of the cover glass 47 in an optical axis direction.

Further, since the positioning is easily performed in this way, it is possible to simplify the attaching process of the cover glass 47.

Figure 13:
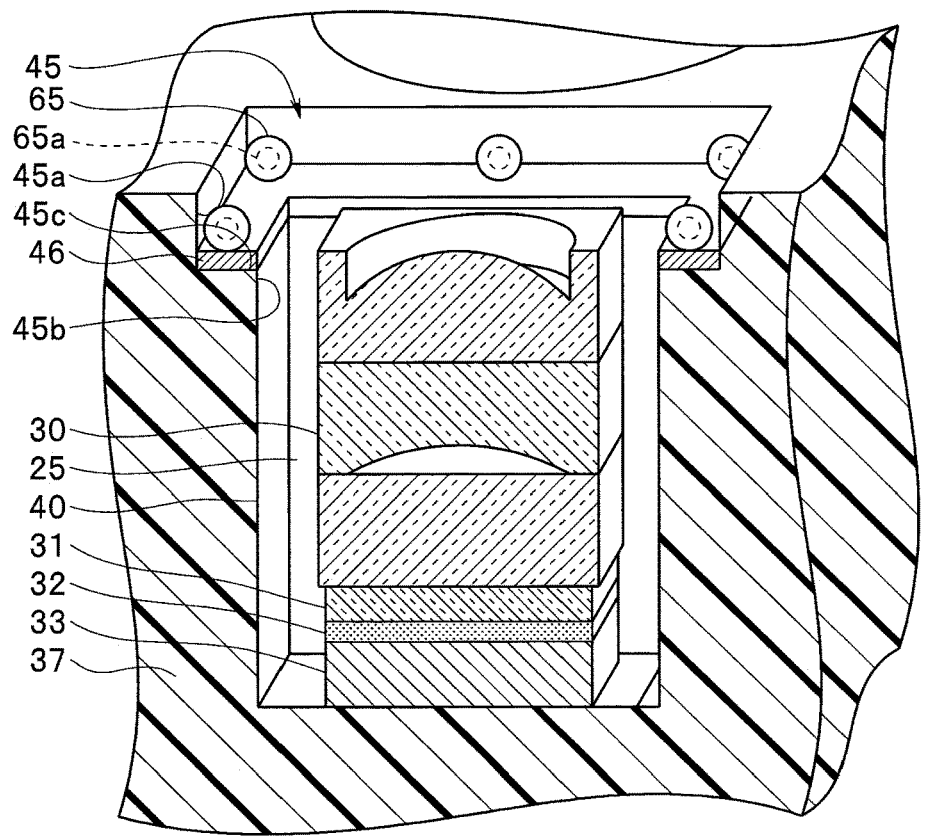
FIG. 13 is a perspective view showing a principal part of a distal end frame according to a seventh modification.
Figure 14:
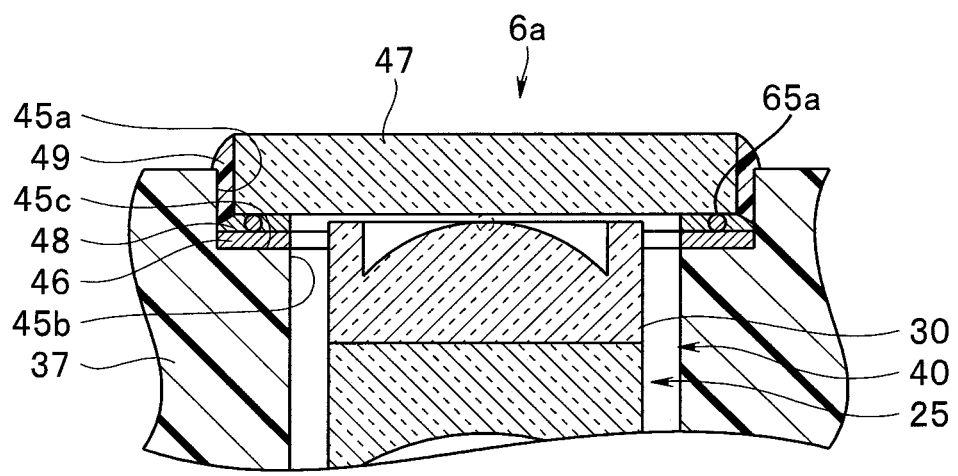
FIG. 14 is a cross-sectional view showing a holding structure of an observation window according to the seventh modification.

For example, as shown in FIG. 13 and FIG. 14, in a configuration in which the metal layer 46 is provided on the flat surface 45c, a solder ball 65 that wraps a rigid spherical core 65a composed of copper or resin in an interior can be used as a solder material that forms the solder layer 48. By this configuration, it is possible to appropriately perform the positioning of the cover glass 47 in the optical axis direction relative to the flat surface 45c, using the core 65a existing in the interior of the formed solder layer 48 as a spacer.

Further, since the positioning is easily performed in this way, it is possible to simplify the attaching process of the cover glass 47.

Figure 15:
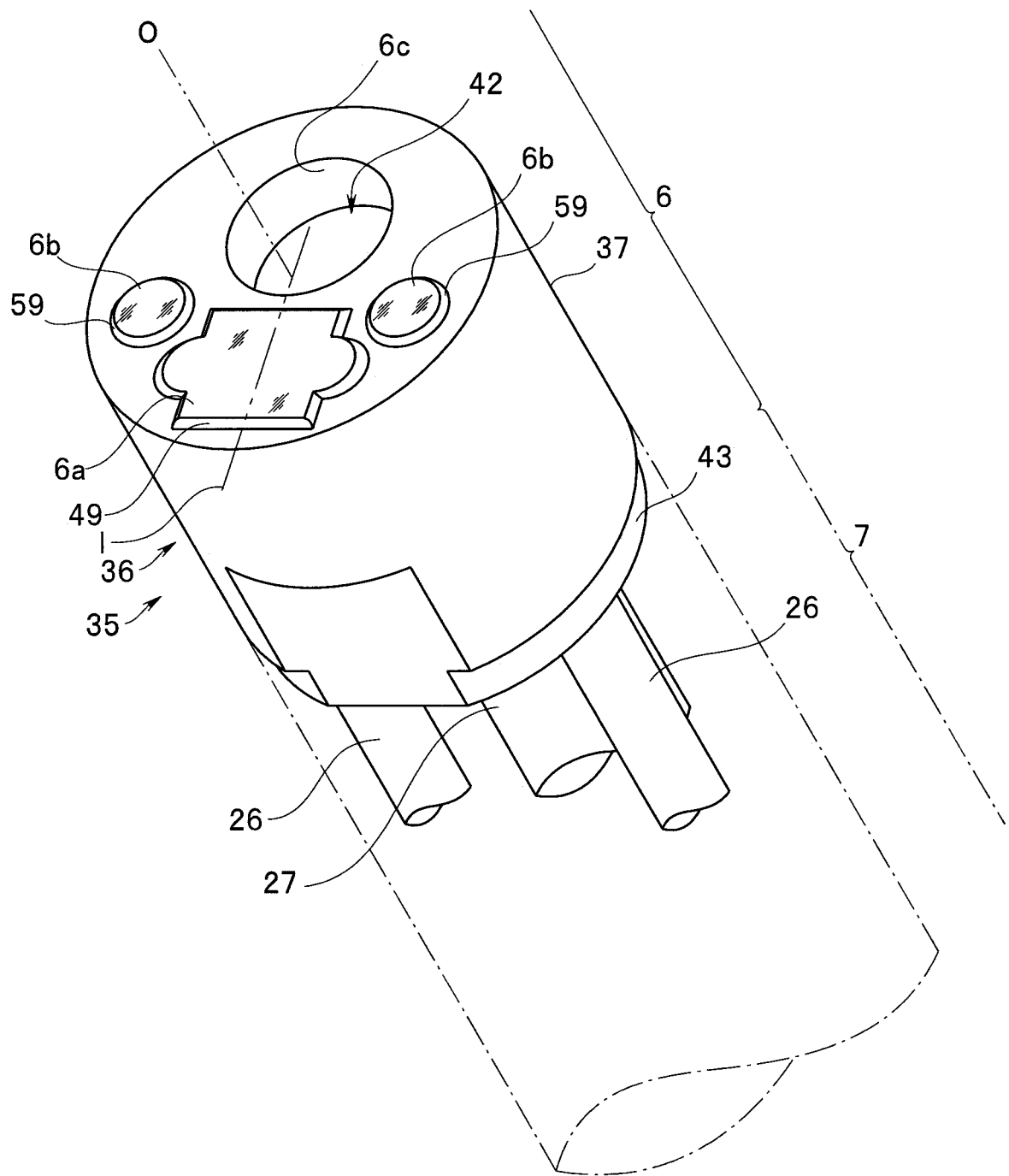
FIG. 15 is a perspective view of a distal end unit according to an eighth modification.
Figure 16:
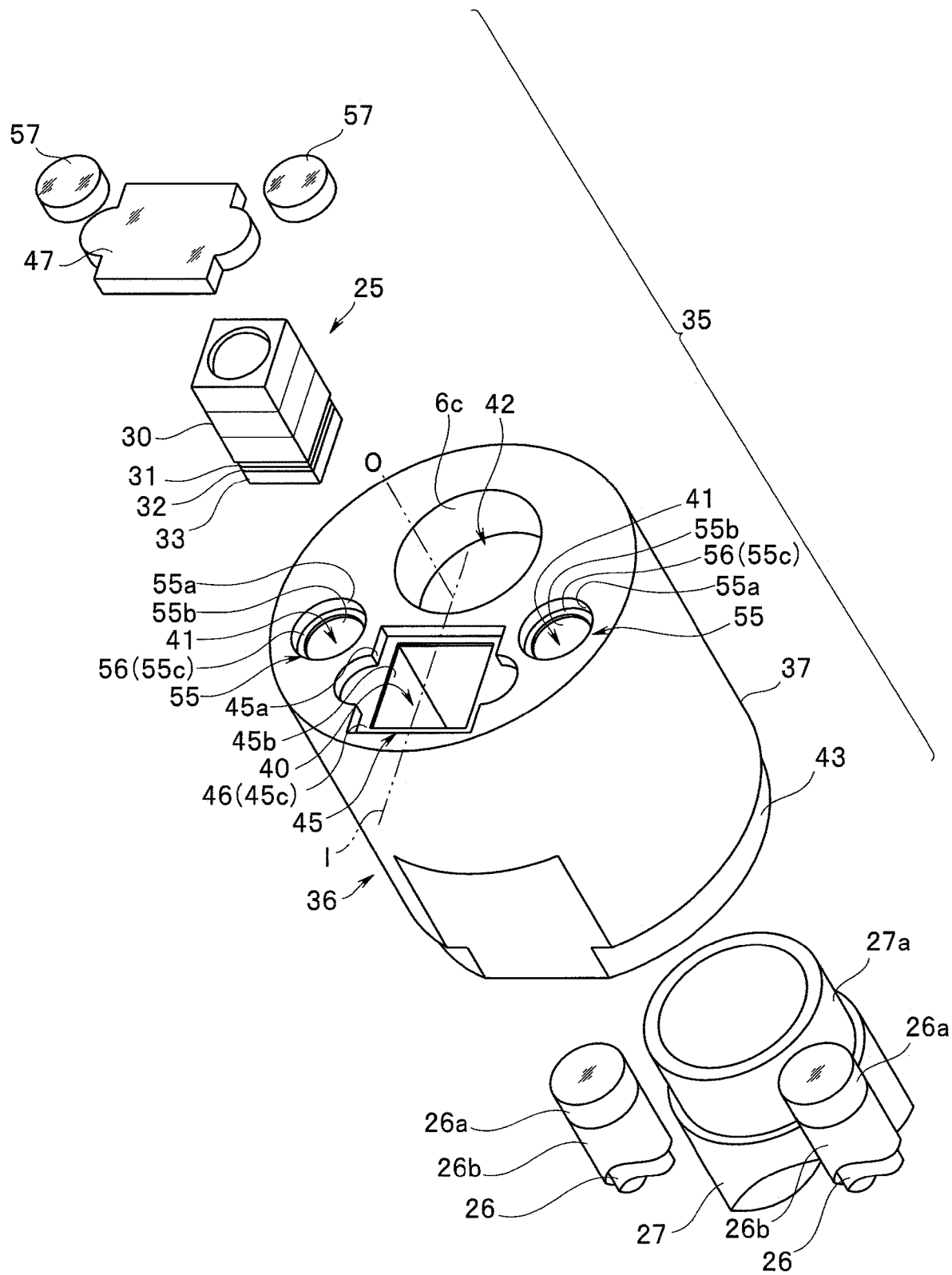
FIG. 16 is an exploded perspective view of the distal end unit according to the eighth modification.

For example, as shown in FIG. 15 and FIG. 16, parts of the first inner circumference surface 45a and the flat surface 45c can be expanded outward, and the cover glass 47 can be formed in a shape corresponding to the expansion shape. By this configuration, it is possible to expand an effective area of the solder layer 48, and to adequately hold the cover glass 47 on the distal end frame 36 at a higher bonding strength.

In this case, by forming expanded regions of the first inner circumference surface 45a and the flat surface 45c in a direction perpendicular to a virtual straight line 1 connecting a center of the channel opening portion 6c and a center of the observation opening portion 45, it is possible to efficiently form the expanded regions on the narrow distal end surface, using dead spaces.

Figure 17:
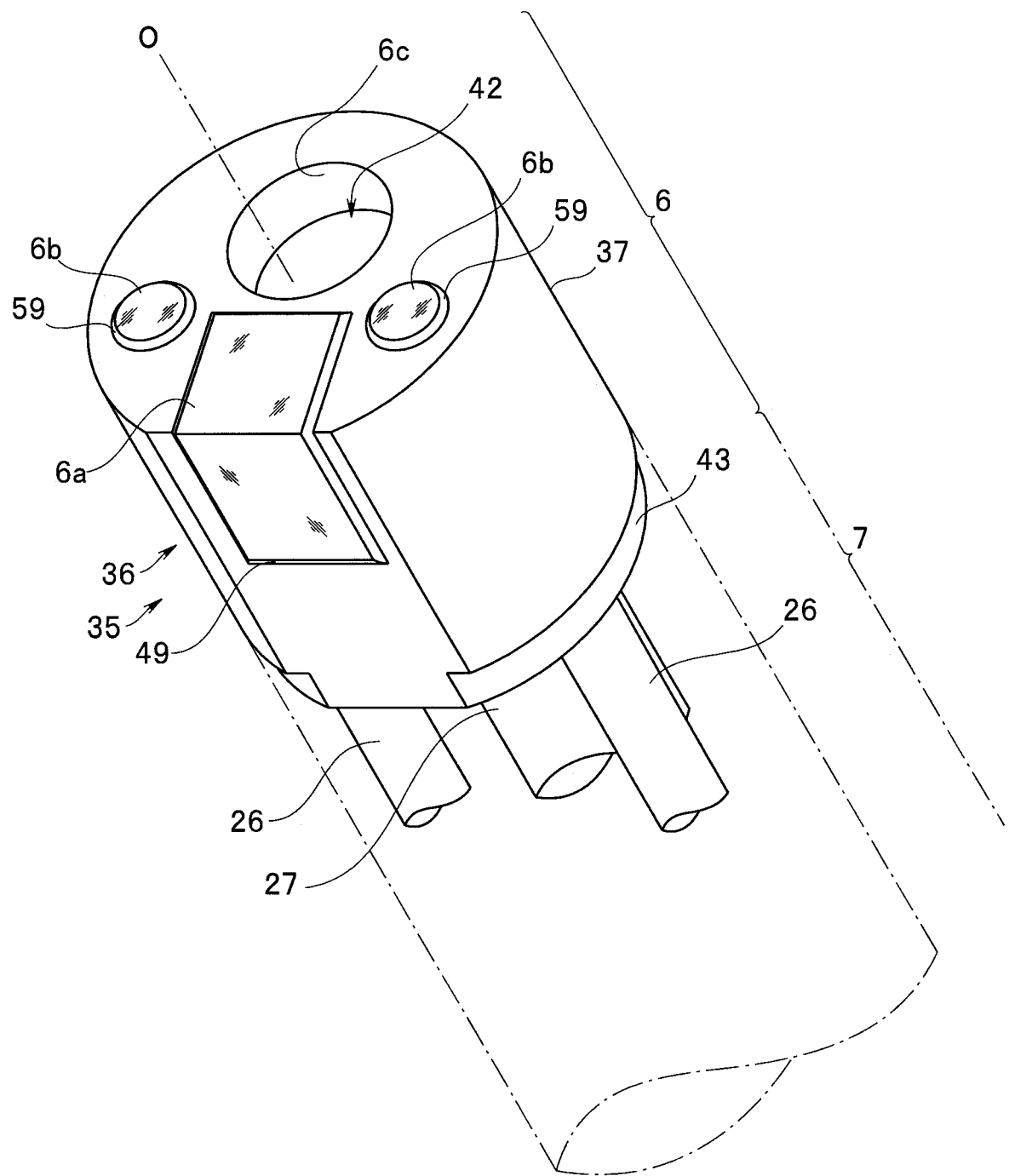
FIG. 17 is a perspective view of a distal end unit according to a ninth modification.
Figure 18:
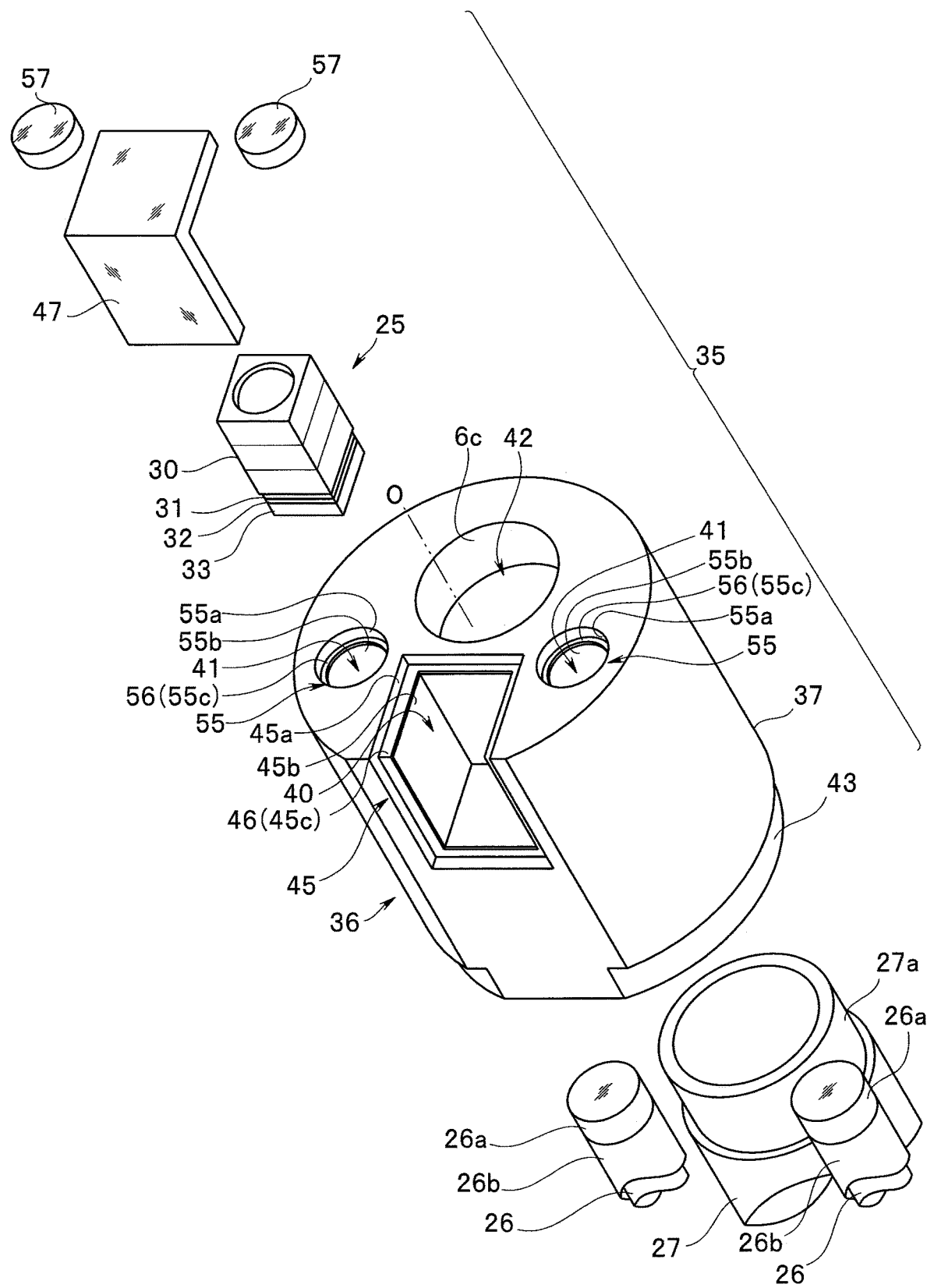
FIG. 18 is an exploded perspective view of the distal end unit according to the ninth modification.

For example, as shown in FIG. 17 and FIG. 18, the observation opening portion 45 can be formed from the distal end surface to a side surface of the distal end frame body 37. In this case, the cover glass 47 is formed in an L-shape corresponding to an opening shape of the observation opening portion 45. By this configuration, it is possible to exclude a part of a side wall constructing the image pickup unit containing room 40, at region on an outer circumference surface side of the distal end frame body 37. Accordingly, a thickness for forming the side wall is unnecessary, and it is possible to realize reduction in the diameter of the distal end frame 36 by a length equivalent to the thickness.

Further, it is possible to increase a bonding area of the cover glass 47, and therefore, it is possible to enhance a bonding hardness of the cover glass 47.

Note that it is preferable to form a light blocking film or the like on the cover glass 47 at a region covering a side portion of the observation opening portion 45 for preventing stray light from entering the image pickup unit 25 from the side in the configuration.

Figure 19:
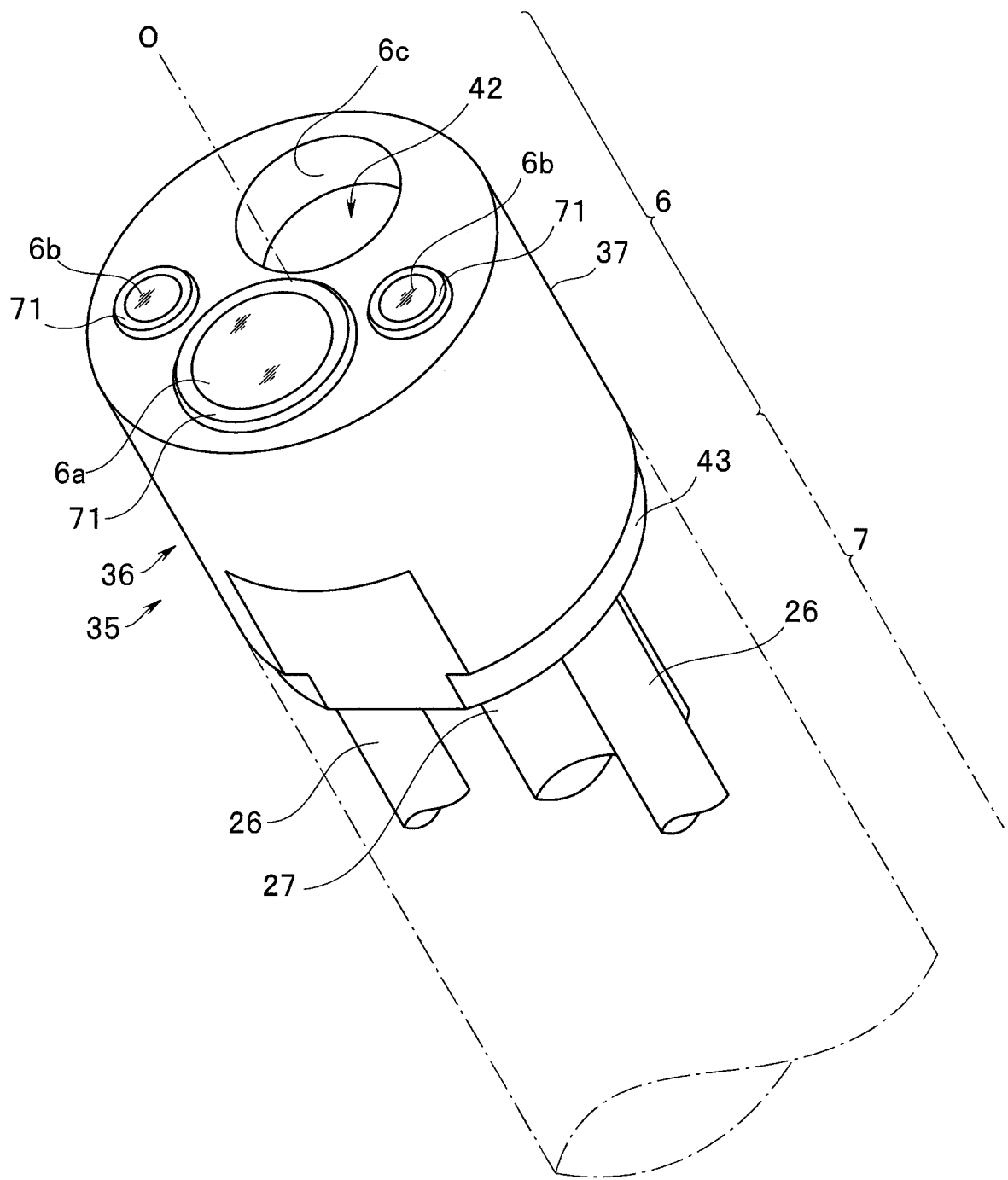
FIG. 19 is a perspective view of a distal end unit according to a tenth modification.
Figure 20:
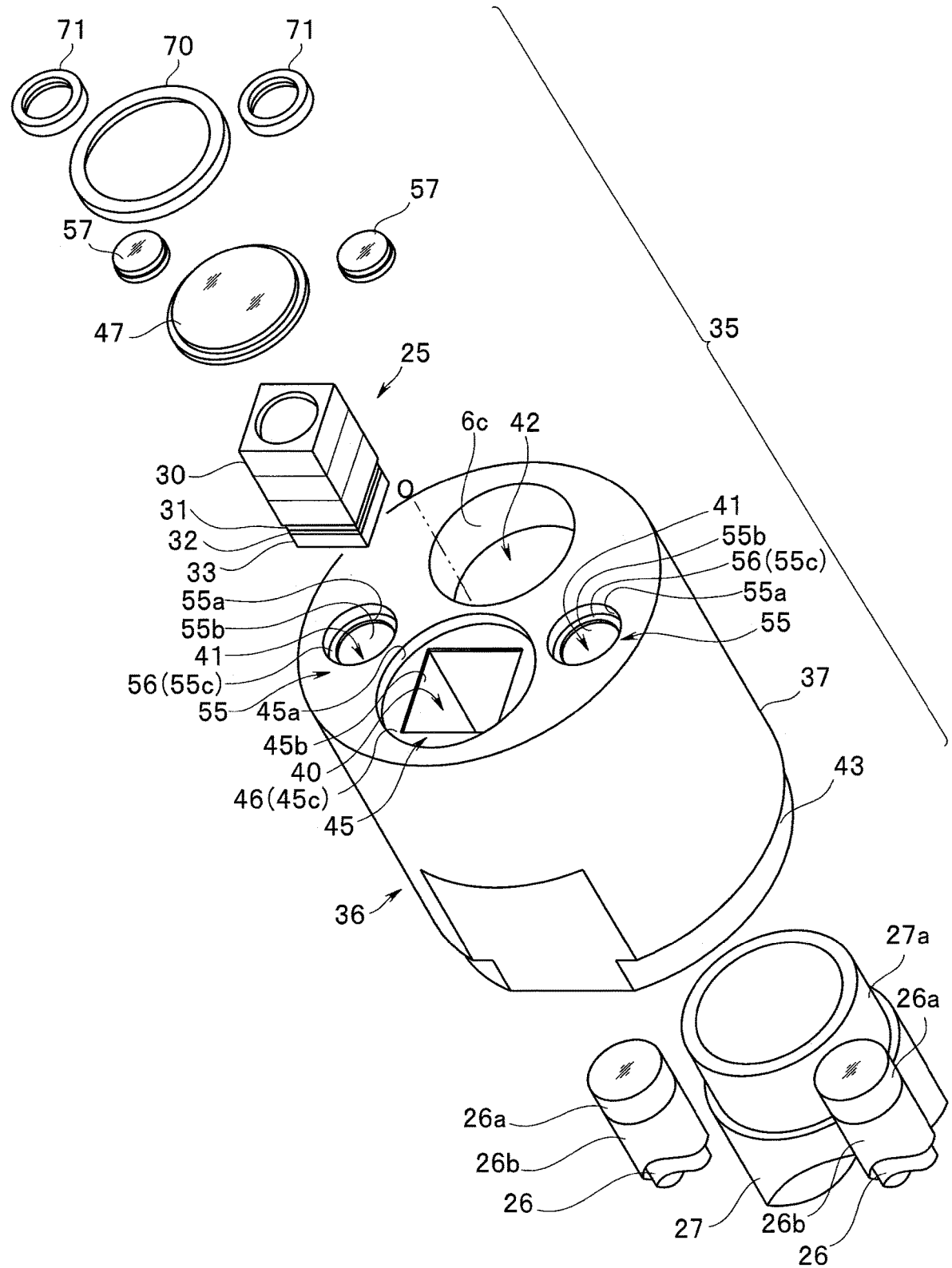
FIG. 20 is an exploded perspective view of the distal end unit according to the tenth modification.
Figure 21:
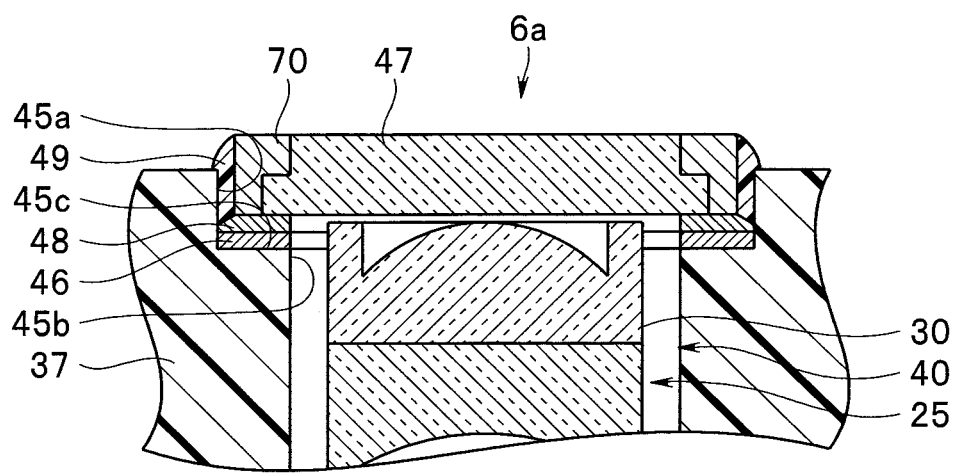
FIG. 21 is a cross-sectional view showing a holding structure of an observation window according to the tenth modification.

For example, as shown in FIG. 19 to FIG. 21, it is possible to indirectly perform the holding of the cover glasses 47, 57 using the solder layers 48, 58, through holding frames 70, 71. In this case, the holding frames 70, 71 are configured by ring-shaped members that are formed so as to cover edge portions and outer circumference surfaces of distal end surfaces of the cover glasses 47, 57 and that are composed of a metal material such as stainless. Further, the holding frames 70, 71 are bonded to the solder layers 48, 58 in a state where the cover glasses 47, 57 are attached, and thereby, hold the cover glasses 47, 57.

By this configuration, it is possible to reinforce peripheries of the cover glasses 47, 57, and to enhance impact resistance.

Figure 22:
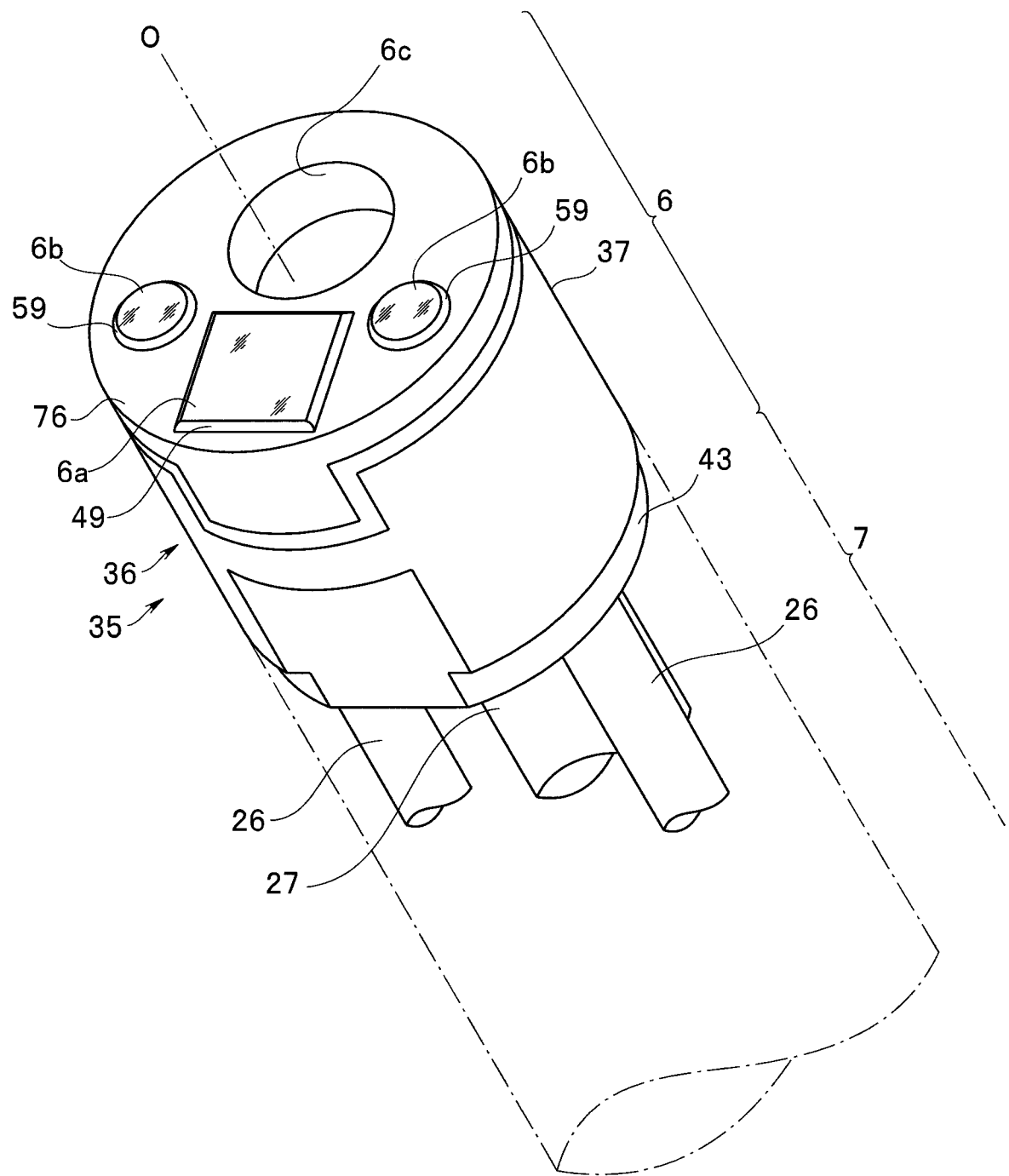
FIG. 22 is a perspective view of a distal end unit according to an eleventh modification.
Figure 23:
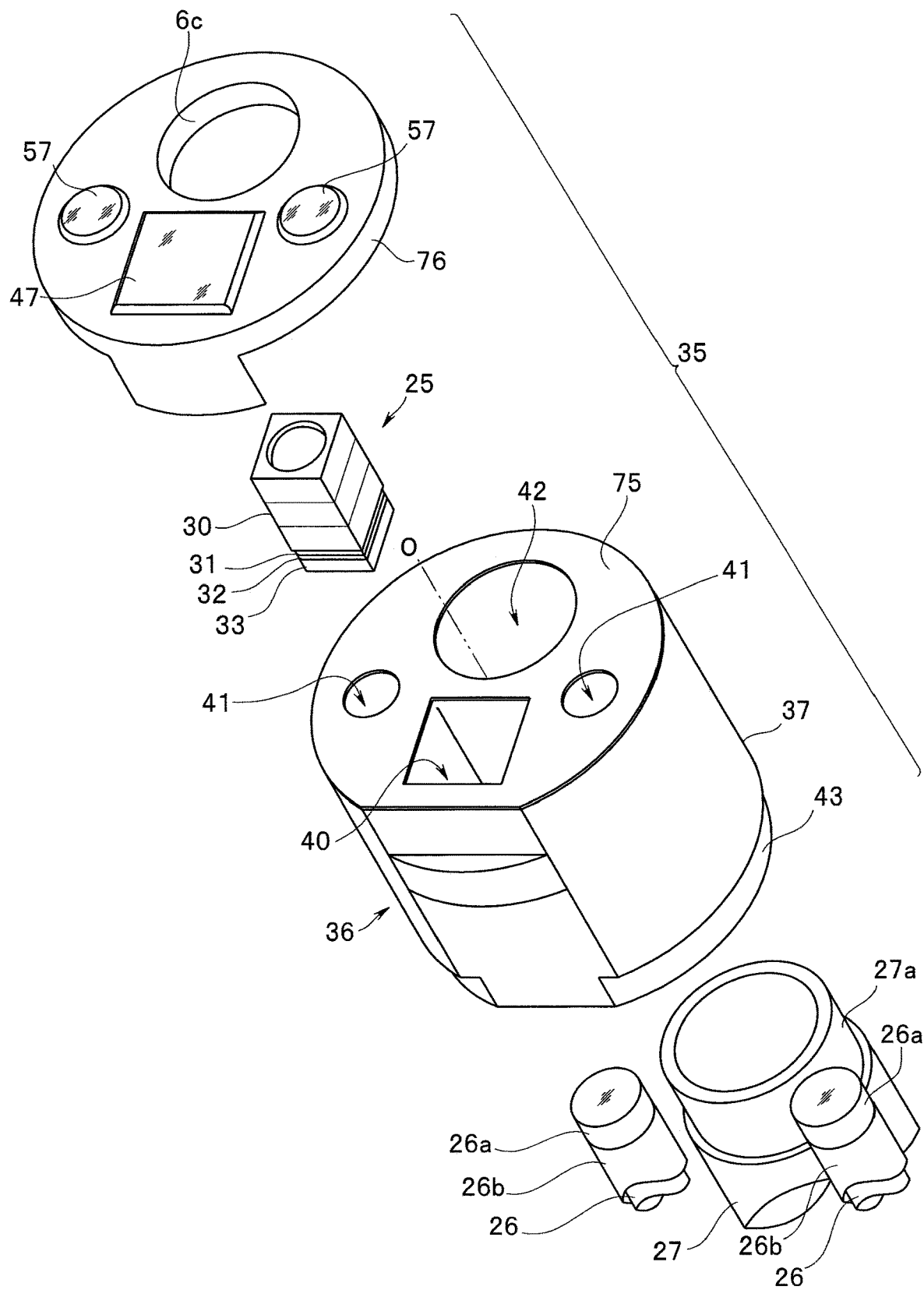
FIG. 23 is an exploded perspective view of the distal end unit according to the eleventh modification.

For example, as shown in FIG. 22 and FIG. 23, a metal layer 75 can be formed on a roughly whole region of the distal end surface of the distal end frame body 37, a holding frame 76 covering the roughly whole region of the distal end surface of the distal end frame body 37 can be provided, the respective cover glasses 47, 57 can be integrally held on a solder layer (not illustrated) through the holding frame 76, and the solder layer can be covered by an adhesive layer 77.

Note that the present invention is not limited to the embodiment and the respective modifications described above, various modifications and alterations can be made, and the modifications and alterations are included in the technical scope of the present invention.

For example, in the above embodiment and the like, the distal end unit of the front-viewing endoscope in which the observation window 6a, the illumination window 6b and the like are disposed in the direction of the insertion axis O has been described as an example, but the present invention can be applied to a distal end unit of a side-viewing endoscope in which the observation window, the illumination window and the like are disposed in a direction intersecting with the insertion axis O.

Further, in the above embodiment and the like, the configuration in which the light guide 26 is held as a light source in the light source containing room 41 has been described as an example, but for example, the light source may be a light-emitting device or the like.

Needless to say, components of the above embodiment and components of the respective modifications may be appropriately combined.

What is claimed is:

1. A distal end unit for use with an endoscope, the distal end unit comprising:
    a distal end frame body comprising resin, the distal end frame body including a cavity extending from a distal end surface of the distal end frame body toward a proximal end of the distal end frame body, the cavity comprising:
        a first inner circumferential surface;
        a second inner circumferential surface having a second periphery shorter than a first periphery of the first inner circumferential surface, the second inner circumferential surface located proximally relative to the first inner circumferential surface;
        a flat surface connecting the first inner circumferential surface and the second inner circumferential surface; and
        a groove provided on the flat surface;
    a metal plating layer provided on the flat surface and in the groove;
    a cover glass disposed in an opening of the cavity to cover a first portion of the metal plating layer such that a second portion of the metal plating layer between the first inner circumferential surface and an outer peripheral surface of the cover glass is not covered by the cover glass;
    solder bonding the cover glass to the metal plating layer; and
    an adhesive disposed between the first inner circumferential surface and the outer peripheral surface of the cover glass to cover the second portion of the metal plating layer.

2. The distal end unit according to claim 1, further comprising an image pickup unit disposed within an interior of the cavity.

3. The distal end unit according to claim 2, wherein the image pickup unit comprises a stack lens and an image pickup device.

4. The distal end unit according to claim 1, further comprising a light source disposed within an interior of the cavity.

5. The distal end unit according to claim 4, wherein the light source is a light guide.

6. The distal end unit according to claim 1, wherein cover glass has a distal surface protruding distally relative to the distal end surface of the distal end frame body surrounding the opening of the cavity.

7. The distal end unit according to claim 1, wherein the cover glass contacts with each of the metal plating layer, the solder and the adhesive.

8. The distal end unit according to claim 1, wherein the groove is recessed from the flat surface toward a proximal direction of the distal end frame body.

9. The distal end unit according to claim 1, wherein the groove comprises a first groove, and further comprising a second groove formed in the metal plating layer, wherein the second groove is located within the first groove.

10. The distal end unit according to claim 9, wherein the solder is disposed in at least the second groove.

11. An endoscope comprising:
    an insertion portion;
    a distal end unit provided in the insertion portion, the distal end unit comprising:
        a distal end frame body comprising a resin the distal end frame body including a cavity extending from a distal end surface of the distal end frame body toward a proximal end of the distal end frame body, the cavity comprising:
            a first inner circumferential surface;
            a second inner circumferential surface having a second periphery shorter than a first periphery of the first inner circumferential surface, the second inner circumferential surface located proximally relative to the first inner circumferential surface;
            a flat surface connecting the first inner circumferential surface and the second inner circumferential surface; and
            a groove provided on the flat surface;
        a metal plating layer provided on the flat surface and in the groove;
        a cover glass disposed in an opening of the cavity to cover a first portion of the metal plating layer such that a second portion of the metal plating layer between the first inner circumferential surface and an outer peripheral surface of the cover glass is not covered by the cover glass;
        solder bonding the cover glass to the metal plating layer; and
        an adhesive disposed between the first inner circumferential surface and the outer peripheral surface of the cover glass to cover the second portion of the metal plating layer.

12. The endoscope according to claim 11, wherein the cavity includes a proximal wall, the endoscope further comprising an image pickup unit disposed in an interior of the cavity.

13. The endoscope according to claim 11, further comprising a light source disposed in the cavity.

14. The endoscope according to claim 11, wherein the cover glass contacts with each of the metal plating layer, the solder and the adhesive.

15. The endoscope according to claim 11, wherein the groove is recessed from the flat surface toward a proximal direction of the distal end frame body.

16. The endoscope according to claim 15, wherein the metal plating layer is recessed from the flat surface toward the proximal direction of the distal end frame body.

17. The endoscope according to claim 11, wherein the metal plating layer is arranged on each of the flat surface and on an interior surface of the groove.

18. The endoscope according to claim 11, wherein
    the groove comprises a first groove, and
    further comprising a second groove formed in the metal plating layer, wherein the second groove is located within the first groove.

19. The distal end unit of the endoscope according to claim 18, wherein the solder is disposed in at least the second groove.

20. A distal end unit for use with an endoscope, the distal end unit comprising:
    a distal end frame body comprising resin, the distal end frame body including a cavity extending from a distal end surface of the distal end frame body toward a proximal end of the distal end frame body, the cavity comprising:
a first inner circumferential surface;
a second inner circumferential surface having a second periphery shorter than a first periphery of the first inner circumferential surface, the second inner circumferential surface located proximally relative to the first inner circumferential surface;
a flat surface connecting the first inner circumferential surface and the second inner circumferential surface; and
a groove provided on the flat surface;
a metal plating layer provided on the flat surface and in the groove;
a cover glass covering a first portion of the metal plating layer such that a space is formed between a second portion of the metal plating layer and at least an outer peripheral surface of the cover glass;
solder bonding the cover glass to the metal plating layer; and
an adhesive disposed in the space.

* * * * *